United States Patent
Tseng

(10) Patent No.: US 7,097,103 B2
(45) Date of Patent: Aug. 29, 2006

(54) METHOD OF AUTOMATICALLY DETECTING A TEST RESULT OF A PROBE ZONE OF A TEST STRIP

(76) Inventor: Wen-Chao Tseng, 56, Min-Chu St., U-Feng Hsiang, Taichung (TW)

( * ) Notice: Subject to any disclaimer, the term of this patent is extended or adjusted under 35 U.S.C. 154(b) by 244 days.

(21) Appl. No.: 10/443,075

(22) Filed: May 22, 2003

(65) Prior Publication Data
US 2004/0232239 A1 Nov. 25, 2004

(51) Int. Cl.
*G06K 7/10* (2006.01)
*G06K 15/00* (2006.01)

(52) U.S. Cl. .................... 235/462.13; 235/462.01; 235/462.15; 235/375; 235/494; 422/58; 435/4

(58) Field of Classification Search .......... 235/462.01, 235/462.04, 462.07, 462.08, 462.09, 462.13, 235/462.15, 454, 486, 494, 375; 422/55, 422/56, 58, 61, 82.05; 435/4, 805
See application file for complete search history.

(56) References Cited

U.S. PATENT DOCUMENTS

| 5,281,395 | A | * | 1/1994 | Markart et al. ......... 422/82.05 |
| 5,493,107 | A | * | 2/1996 | Gupta et al. ............... 235/375 |
| 5,902,982 | A | * | 5/1999 | Lappe ........................ 235/375 |
| 5,929,422 | A | * | 7/1999 | Lappe .................... 235/462.13 |
| 6,036,092 | A | * | 3/2000 | Lappe .................... 235/462.13 |
| 6,315,951 | B1 | * | 11/2001 | Markart ....................... 422/61 |
| 6,319,665 | B1 | * | 11/2001 | Zwanziger et al. ........... 422/55 |
| 6,394,952 | B1 | * | 5/2002 | Anderson et al. .............. 435/4 |
| 6,702,988 | B1 | * | 3/2004 | Sagona et al. ................ 422/61 |
| RE38,509 | E | * | 5/2004 | Lappe .................... 235/462.13 |
| 6,770,487 | B1 | * | 8/2004 | Crosby ........................ 422/56 |
| 2004/0087009 | A1 | * | 5/2004 | Schembri ................. 435/287.2 |

FOREIGN PATENT DOCUMENTS

EP 0 837 320 A2 * 4/1998

* cited by examiner

*Primary Examiner*—Jared J. Fureman

(57) ABSTRACT

Embodiments of a method and/or apparatus for automatically detecting a test result of a probe zone of a test strip are provided.

16 Claims, 7 Drawing Sheets

METHOD OF AUTOMATICALLY DETECTING A TEST RESULT OF A PROBE ZONE OF A TEST STRIP

BACKGROUND OF THE INVENTION

1. Field of the Invention

The present invention relates to a method for detecting a test result of each probe zone of a test strip, and more particularly to a method for detecting a test result of each probe zone of a test strip via an image capturing/processing technology.

2. Description of the Prior Art

Over the past decade, there has been an increased need and demand for analysis of various biological specimens, for purposes ranging from pregnancy testing to drug analysis. Considerable time and effort has been expended by way of devising systems and analytic techniques to ensure reliable testing and accurate results.

Moreover, with increasing rise in the use of abuse-type drugs, the need for detecting and identifying those drugs and their metabolites is becoming more important. With this need, many more tests are required to monitor the use of abuse-type drugs.

Thin layer chromatography (TLC) screening procedures for detecting drugs in urine require the careful preparation of a test specimen and then a skillful application of that test specimen to a plate placed into a developing chamber. Once the plate is removed from the chamber and dried, it is sprayed with visualization reagents. Location and color of spots are compared with those of known standards. Qualitative judgements are made as to the presence of various drugs in the unknown sample. The procedure is tedious, time consuming and requires skilled personnel to interpret the results.

The EMIT (Enzyme Multiplied Immuno-chemical Test) procedure is a semi-quantitative immuno-assay for drugs of abuse in biological fluids. The laboratory test requires trained technicians to perform and the equipment necessarily costs several thousands of dollars.

The RIA (Radio-Immuno-Assay) procedure is a sensitive and quantitative laboratory procedure for detecting drugs of abuse. The various immunochemicals are labeled with radioactive compounds and require special care in their use and disposal. A license is required from the government to use this laboratory procedure because of the presence of radioactive materials. The GLC (Gas-Liquid Chromatography) procedure can provide the highest degree of accuracy in drug analysis. However, the necessary equipment is expensive and the procedure is complicated. Consequently, highly trained personnel are required for its use.

Each of these well-known procedures requires skilled technicians and relatively sophisticated equipment. Consequently, the testing procedure is necessarily expensive.

However, the increase of drug abuse has increased a need for new methods of analyzing drug residues in physiological fluid. A drug abuse test paper for testing the presence or absence of drugs in a fluid specimen collected from a test subject is developed. The drug abuse test paper is sensitive to specific drugs of abuse in the fluid specimen collected from the test subject, and has a lack of color change indicating a positive response to a specific drug of abuse in the fluid specimen, and representing the specific drug of abuse present therein. While, a color change indicates a negative response to the specific drug of abuse, representing the specific drug of abuse absent in the fluid specimen.

An introduction of various color patterns occurring on the drug abuse test strip under various testing situations is provided herein. Firstly, referring to FIG. 1A, which is a schematic top view of the drug abuse test strip 10 prior to testing the fluid specimen collected from the test subject. The drug abuse test strip 10 is blank and no color pattern displayed thereon prior to testing the fluid specimen. The dotted lines 11 through 16 respectively represent a probe zone of the drug abuse test strip 10. The top probe zone of the drug abuse test strip 10 corresponding to the site of dotted line 11 displays a color change in response to the fluid specimen, which is used to indicate whether the amount of the fluid specimen is sufficient to move through all probe zones of the drug abuse test strip 10 by capillary action. The color line displayed on the top probe zone is called control line. The other probe zones of the drug abuse test strip 10 corresponding to the sites of dotted lines 12 through 16 respectively display a color change in response to a respective drug of abuse presenting in the fluid specimen. The color lines displayed on these probe zones are called target lines.

Referring to FIG. 1B, which shows a color pattern of the drug abuse test strip 10 having no color change occurring in the top probe zone represented by the dotted line 11, which is under a testing situation that the amount of the fluid specimen is not sufficient to assure the fluid specimen moves through all probe zones of the drug abuse test strip 10. Therefore, in accordance with the color pattern consisting of solid lines 14 through 16 shown in FIG. 1B, the drugs of abuse presenting in the fluid specimen cannot completely detected and identified. Referring to FIG. 1C, which shows a color pattern of the drug abuse test strip 10 having only one color line 11 displayed in the top probe zone of the drug abuse test strip 10. It means the top probe zone has a positive response in response to the fluid specimen. The amount of the fluid specimen is sufficient to pass through all probe zones on the drug abuse test strip 10. All other probe zones represented by the dotted lines 12 through 16 have positive responses to the fluid specimen, and all drugs of abuse corresponding to these probe zones present in the fluid specimen. Referring to FIG. 1D, which shows a color pattern of the drug abuse test strip having color lines 11, 12 and 15 displayed in the top probe zone and some other probe zones of the drug abuse test strip 10, which means the top probe zone 11 has a positive response to the fluid specimen, indicating the amount of the fluid specimen is sufficient, and the probe zones represented by the color lines 12 and 15 have a negative response to the fluid specimen, indicating that the absence of the drugs of abuse corresponding to these two probe zones in the fluid specimen. On the contrary, the probe zones represented by the dotted lines 13, 14 and 16 have a positive response to the fluid specimen, indicating that the presence of the drugs of abuse corresponding to these three probe zones in the fluid specimen.

The top probe zone on the drug abuse test strip 10 has a positive response in response to the specimen fluid, a color response occurs. That is, the control line 11 would display thereon. One of the other probe zones of the drug abuse test strip 10 has a positive response in response to a specific drug of abuse of the fluid specimen, there is no color response occurs on the probe zone. It means the specific drug of abuse is present in the fluid specimen, and there is a highly content of the specific drug of abuse in the fluid specimen. However, one of the other probe zones of the drug abuse test strip 10 has a negative response in response to a specific drug of abuse of the fluid specimen, a color response, i.e. target line, is displayed on the probe zone. The color shade of the target line can be used to monitor the content of the specific drug of abuse or even represents absence of the specific drug of abuse in the fluid specimen. The color shade of each of the target lines 12 to 16 is inversely proportional to the content of a specific drug of abuse to be detected in the fluid specimen. The higher the content of the specific drug of abuse is, the lighter the color shade of the target line is. The content of the specific drug of abuse is inversely proportional to the color intensity, i.e. the shade of color, of the target line. It is difficult to visually determine what certain level of the color shade of the target line representing the presence of the specific drug of abuse to be detected. Therefore, it is not convincing for concluding whether the test subject has used abuse-type drugs.

Accordingly, it is an intention to provide means capable of detecting and identifying the presence or absence of drugs of abuse in a fluid specimen, which can overcome the problems of the conventional methods.

SUMMARY OF THE INVENTION

It is one objective of the present invention to provide a method of automatically detecting a test result of a probe zone of a test strip, which reads a bar code pattern corresponding to the test strip to obtain setting values of target lines of the test strip, and in accordance with the setting values, determines respective test results of the target lines of the test strip contacting with a test liquid.

It is another objective of the present invention to provide a method of automatically detecting a test result of a probe zone of a test strip, which utilizes an image capturing device associated with an user interface to capture images of a color pattern of the test strip and a corresponding bar code pattern, then decoding the bar code pattern to obtain setting values of target lines of the test strip, and thereby determining the respective test results of the target lines, then directly displaying the test results on the user interface for viewing.

It is still another objective of the present invention to provide a method of automatically detecting a test result of a probe zone of a test strip, which utilizes an image capturing/processing technology associated with an application for image analysis to automatically determine respective test results of target lines of the test strip. The manual operation is eliminated and the detection time is shortened.

In order to achieve the above objectives of this invention, the present invention provides a method of automatically detecting a test result of a probe zone of a test strip. A scanning object including a bar code and a plurality of test strips is provided. The bar code is placed in a predetermined position on the scanning object and the test strips are arranged in sequence on the scanning object not overlapped with the bar code. Each of the test strips has a color pattern including a control line and a plurality of target lines arranged in sequence on the test strip from one end to the other end thereof. The control line and each of the target lines respectively correspond to a probe zone of the test strip. Scanning the scanning object to read a bar code pattern of the bar code and capture images of the test strips. Decoding the bar code pattern of the bar code to obtain information of types of the test strips and thereby a plurality of mapping tables of setting values versus positions of the target lines on the test strip. Each mapping table corresponds to one of the test strip based on the type of the test strip, and each setting value of the mapping table corresponds to the position of one target line of the test strip. Calculating a color response of one target line of the test strip based on the image of the test strip. Comparing the color response of the target line of the test strip with the setting value corresponding thereto derived from the mapping table corresponding to the test strip so as to determine whether the target line has a positive test result or a negative test result.

The present method detects a bar code corresponding to a test strip to obtain the type of the test strip. And, obtaining respective setting values of target lines of the test strip in accordance with a mapping table of the setting values versus the target lines, which is correlated to the type of the test strip. Thereby, determining respective test results of the target lines of the test strip contacting a test liquid by comparing the respective color responses of the target lines with the respective setting values. Hence, the present invention provides an automatic, rapid and accurate method to determine the test result of the probe zone of the test strip.

BRIEF DESCRIPTION OF THE DRAWINGS

The objectives and features of the present invention as well as advantages thereof will become apparent from the following detailed description, considered in conjunction with the accompanying drawings.

DESCRIPTION OF THE PREFERRED EMBODIMENT

The present invention provides a method of automatically detecting a test result of a probe zone of a test strip, which utilizes an image capturing device, such as a scanner, to capture an image of a color pattern having a control line and a plurality of target lines of the test strip, for example a drug-abuse type test paper, and a bar code pattern of a bar code corresponding to the test strip. Decoding the bar code pattern to obtain the type of the test strip, and thereby a mapping table of setting values versus respective target lines of the test strip correlated to is obtained. The type of the test strip determines the test strip detect what kinds of specific components contained in a test liquid. Each setting value represents a threshold of a color response of one of the target lines having a positive test result in response to a specific component of the test liquid. Calculating the color response of the target line of the test strip in accordance with the image of the color pattern of the test strip, and comparing the color response of the target line with the setting value corresponding thereto derived from the mapping table to determine whether the target line has a positive or negative test result. Then, the test result is directly displayed on a user interface associated with the image capturing device. A user can view the test result of each of the target lines of the test strip from the display of the user interface.

Figure 1D:
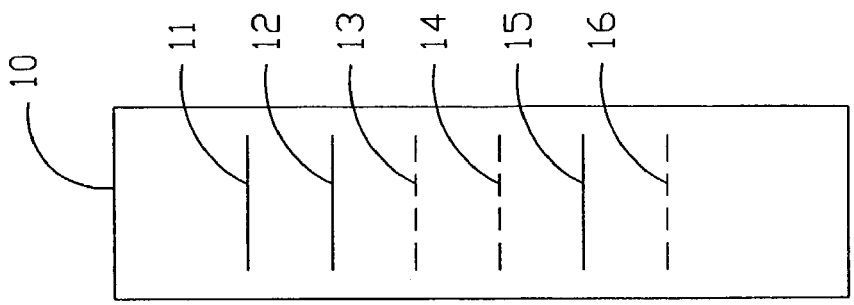
FIG. 1A to FIG. 1D shows schematic top views of a known drug abuse test strip under various testing situations.
Figure 1C:
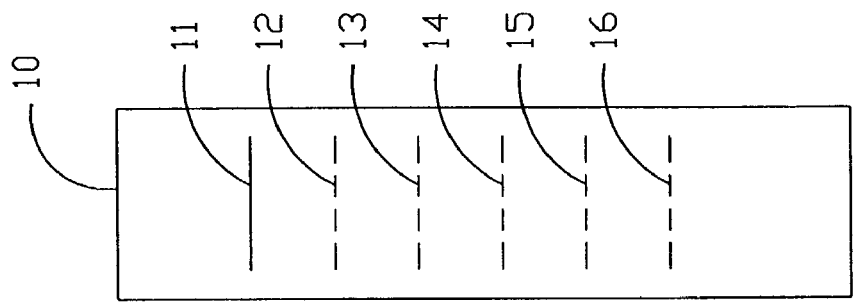
Figure 1B:
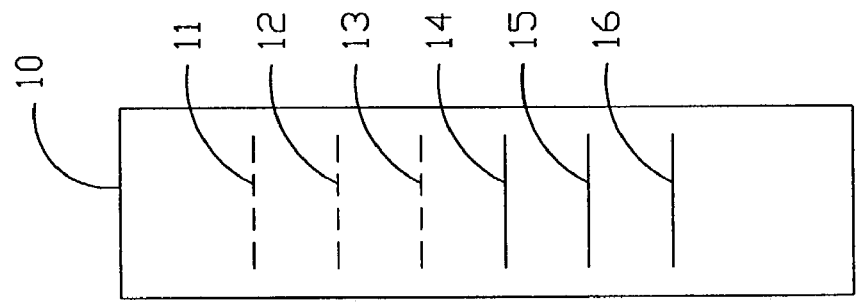
Figure 1A:
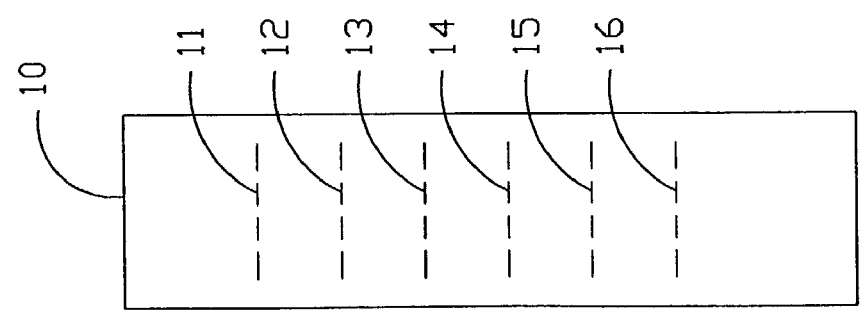
Figure 2:
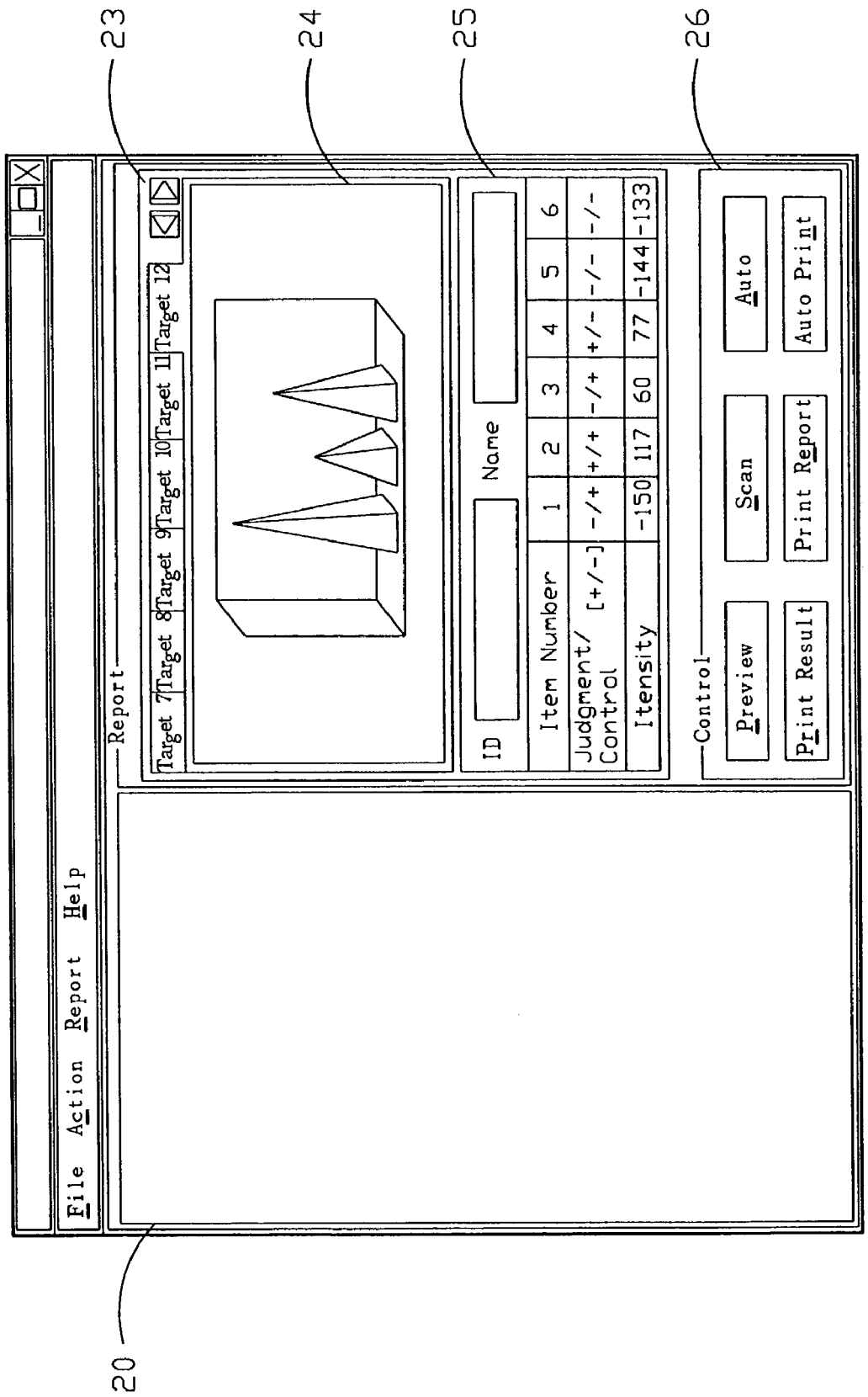
FIG. 2 is a schematic configuration of a user interface utilized in the present invention.
Figure 3A:
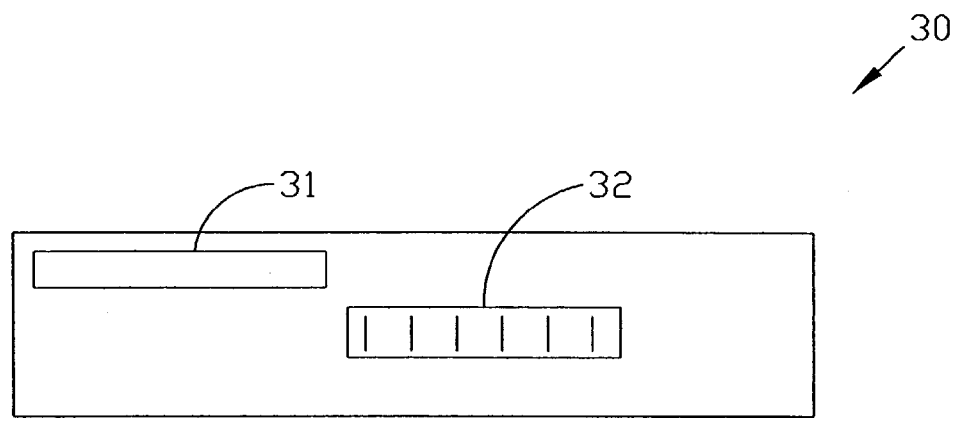
FIG. 3A and FIG. 3B are schematic top views of scanning objects of the present invention.
Figure 3B:
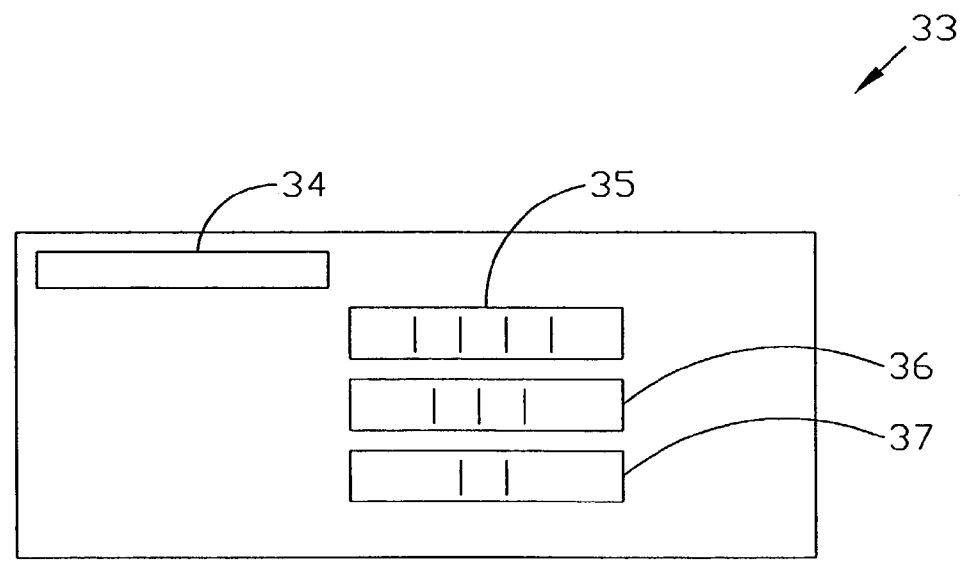

FIG. 2 is a schematic configuration of the user interface associated with the image capturing device utilized in the present invention. An image preview window 20 is displayed on a right side portion of the user interface. The image preview window 20 displays preview images of scanning objects. FIG. 3A and FIG. 3B are schematic top views of the scanning objects of the present invention. The scanning object 30 of FIG. 3A includes a bar code 31 and a test strip 32 having a color pattern including a control line and a plurality of target lines arranged in sequence on the test strip 32 from one end to the other end thereof. The control line has a color change in response to a test liquid tested by the test strip 32 and each of the target lines represents a probe zone having a color change in response to a specific component in the test liquid. The scanning object 33 of FIG. 3B includes a bar code 34 and a plurality of test strips 35, 36 and 37. The bar code 34 is placed in a predetermined position on the scanning object 33 and the test strips 35, 36 and 37 are arranged in sequence on the scanning object 33 not overlapped with the bar code 34. The test strips 32, 35, 36 and 37 shown in FIG. 3A and FIG. 3B can be the drug abuse test paper 10 of FIG. 1. And, the test liquid can be a kind of biological specimen collected from a test subject, such as blood, urine, sweat, and saliva. The user can directly select the preview image of one of the scanning objects on the image preview window 20 to execute a normal scan. Alternately, the user can select the preview images of several scanning objects on the image preview window 20 at one time. The selection order of the preview images would be stored.

A first region for displaying image analysis results 33 is displayed on a left portion of the user interface and used for displaying an image analysis result under a normal scan for the selected image. The display of the image analysis result includes a diagram 24 of image intensity versus image position of the target lines of each of the test strips of the scanning object and a data table 25 of image intensity versus image position of the target lines. The data table 25 also includes an "ID" column for showing an ID number reading from the bar code labeled on the scanning object and a "Name" column corresponding to a test subject whose biological specimen is tested by the test strips of the scanning object. The user can key in the name of the test subject in the "Name" column. In the data table 25, each of the test strips of the scanning object is given an item number in accordance with the sequence of the test strips arranged in the scanning object, wherein each of the test strips only detects one specific component contained in the test liquid. The data table 25 also has a column "(Judgment/Control)" displaying test results of the target lines and control lines of the test strips contacting with the test liquid. "Judgment" displays the test result of the target line of the test strip and "Control" displays the test result of the control line of the test strip. The test result "+/or −" of the target line and control line of the test strip is automatically displayed on the data table 25 by the present method for decoding the bar code pattern of the bar code labeled on the scanning object to obtain the setting value of the target line and comparing the color response of the target line with the setting value to determine the test result. Besides, there are several selection buttons (Target 7, Target 8, Target 9, Target 10, Target 11, Target 12) displayed on a top portion of the first region for displaying image analysis results 23. The order of the selection buttons corresponds to the order of selection of the preview images on the image preview window 20. The user can click one of the selection buttons to switch the displaying of the first region for displaying image analysis result 23.

A second region for displaying function buttons 26 is displayed below the first region for displaying image analysis results 23 on the user interface. The function buttons include a preview button (Preview), a scan button (Scan), an auto button (Auto), a print result button (Print Result), a print report button (Print Report) and an auto print button (Auto Print). The preview button provides an image preview scan function and the scan button provides a normal scan function for the selected preview image. The auto button provides a normal scan for the whole page of preview images displayed on the preview window 20. The print result button (Print Result) provides a function for printing out the image analysis result under the normal scan for the selected preview image. The print report button (Print Report) provides a function for printing out an image under the normal scan for the selected preview image and the image analysis result thereof. The auto print button (Auto Print) provides a function for print out images under the normal scan for the whole page of preview images displayed on the image preview window 20 and the image analysis results thereof.

Figure 4:
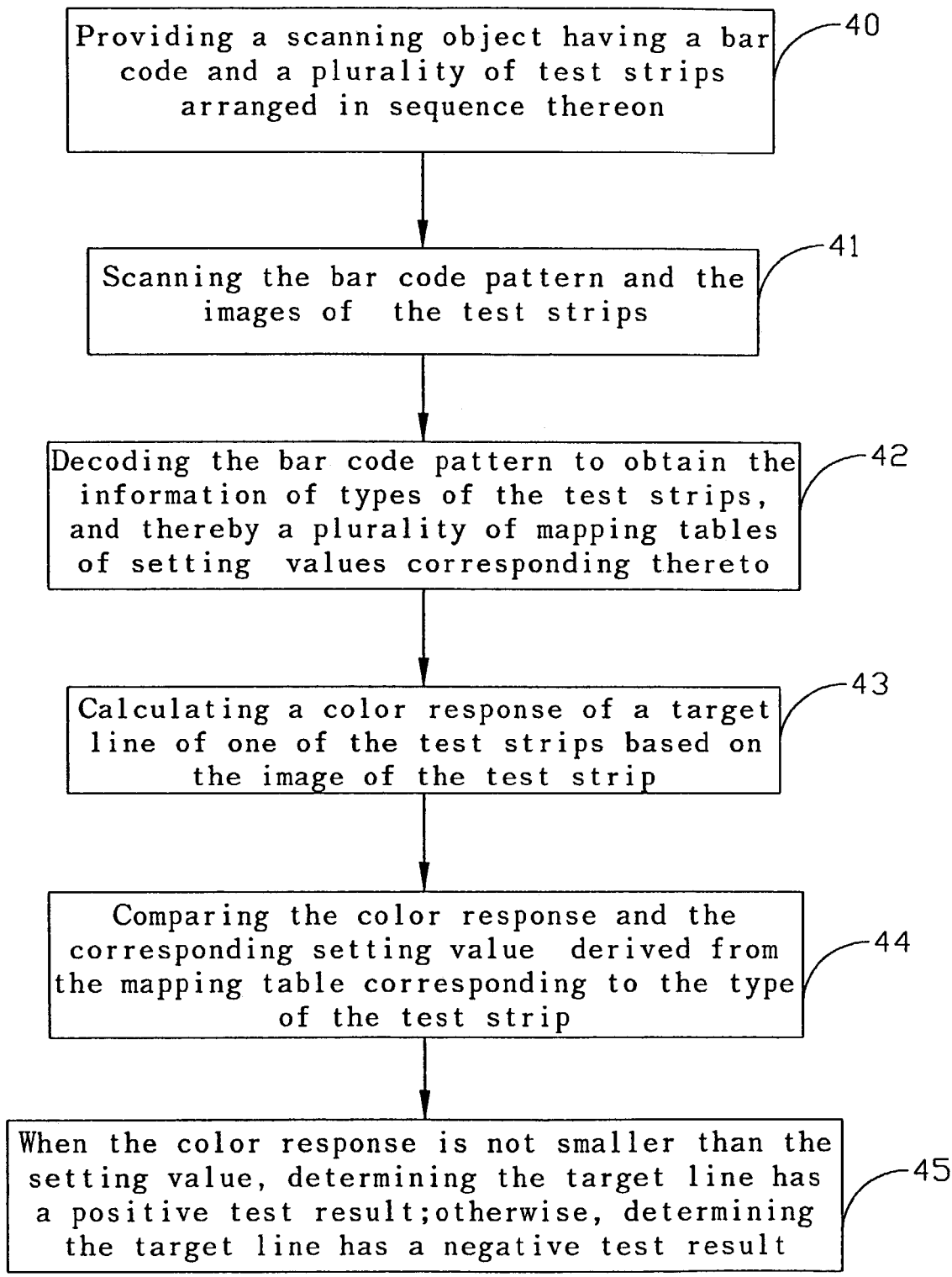
FIG. 4 is a flow chart of the present method according to an embodiment of the present invention.
Figure 5:
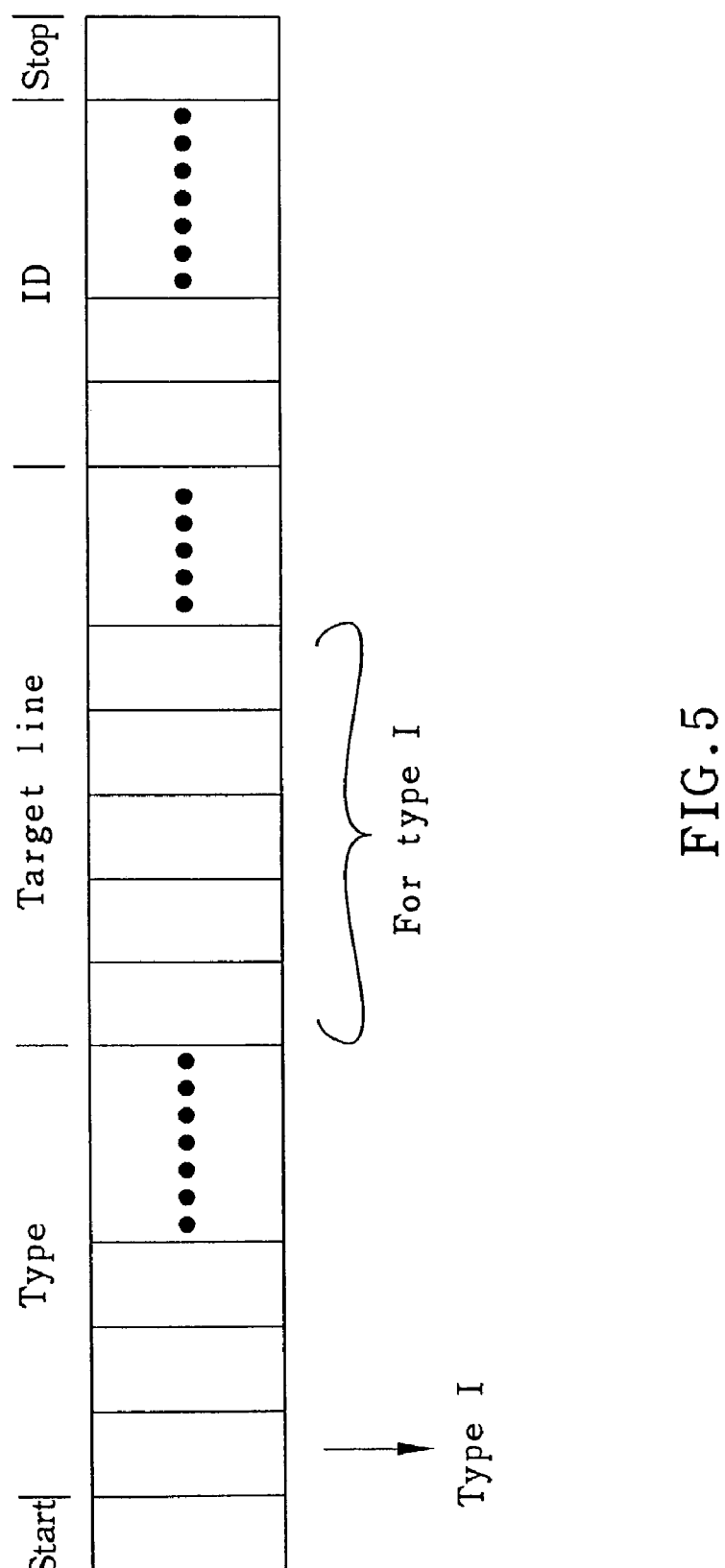
FIG. 5 is a schematic view of a format of a bar code utilized in the embodiment of the present invention.

FIG. 4 is a flow chart of the present method according to an embodiment of the present invention. Initially, at step 40, providing a scanning object having a bar code and a plurality of test strips arranged in sequence thereon. The bar code is placed at a predetermined position on the scanning object and the test strips are arranged in sequence on the scanning object not overlapped with the bar code. Each of the test strips has a color pattern including a control line and a plurality of target lines arranged in sequence on the test strip from one end to the other end thereof. The control line has a color change in response to a test liquid tested by the test strip and each target line representing a probe zone having a color change in response to a specific component in the test liquid. The scanning object can be the scanning object 30 or 32 of FIG. 3A and FIG. 3B. The test strips can be classified to various types in accordance with how many kinds of specific components in the test liquid can be detected by the test strip. The bar code can have a one-dimensional bar code pattern, for example, as shown in FIG. 5, including a "start" bar pattern, a first group of bar patterns corresponding to types of the test strips on the scanning object, each bar pattern of the first group sequentially corresponding to the type of one of the test strips, a plurality of second groups of bar patterns, each second group of bar patterns sequentially corresponding to one of the test strips, and each bar pattern of the second group sequentially corresponding to the position of one of the target lines of the test strip, a third group of bar patterns corresponding to an identification number of the scanning object, and a "stop" bar pattern. Each of the bar patterns of the bar code has a constant code length and is consisted of bars and spaces.

At step 41, scanning the scanning object to read the bar code pattern of the bar code and capture images of the test strips with the image capturing device with a charged-coupled device having R, G, B channels disposed in parallel thereon. Each of the R, G, B channels includes a plurality of sensor cells, and each sensor cell corresponds to a pixel position. Alternately, the present invention can utilize a charge-coupled device with a single channel, such as a charge-coupled device with a red channel, a charge-coupled device with a green channel or a charge-coupled device with a blue channel. Then, at step 42, decoding the bar code pattern of the bar code to obtain information of types of the test strips and thereby a plurality of mapping tables of setting values versus positions of the target lines on the test strip. Each mapping table corresponds to one of the test strips based on the type thereof reading from the bar code, and each setting value of the mapping table corresponds to one specific component to be detected by one target line of the test strip. The setting value is a threshold of a color response of the target line having a positive test result in response to the specific component. When a test strip of type I is detected by reading the bar code, a mapping table I as shown in the following correlated to is obtained.

TABLE I

| Position of target line | 1 | 2 | 3 | 4 | 5 |
|---|---|---|---|---|---|
| Setting value | 50 | 30 | 60 | 55 | 70 |

The mapping table I lists positions of the target lines of the test strip of type I and the respective setting values. Herein, for example, the test strip of type I can detect five specific components in the test liquid, therefore the mapping table I lists the positions of five target lines of the test strip of type I and their respective setting values. The positions of the target lines are based on the sequence of the target lines on the test strip of type I. Hence, the setting value of each target line of the test strip can be obtained by reading the bar code and further by the mapping table correlated to.

Figure 6:
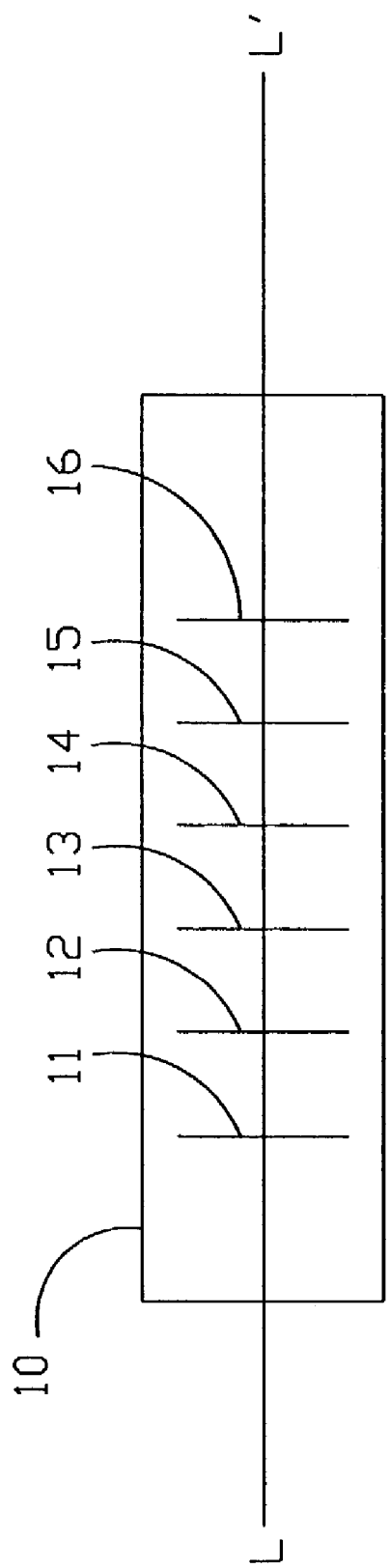
FIG. 6 is a schematic top view of an image of a test strip having a color pattern displayed thereon.
Figure 7:
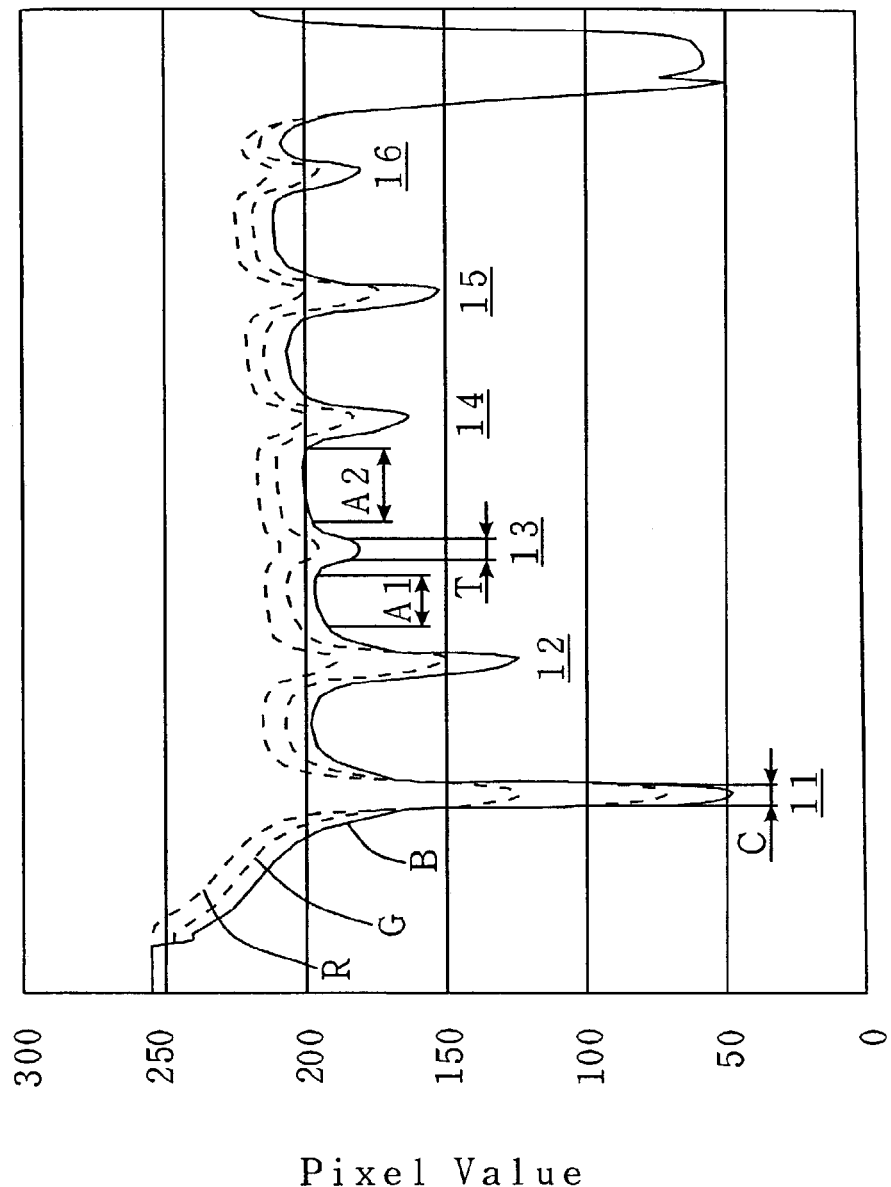
FIG. 7 is a diagram of pixel value versus pixel position established in accordance with one scan line selected from the image of the test strip of FIG. 6.

Following, at step 43, calculating a color response of one of the target lines of the test strip based on the image of the test strip. FIG. 6 is a schematic view of the image of the color pattern of the test strip 10 can be placed on the scanning object. The color pattern of the test strip 10 includes a control line 11 and several target lines 12 to 16. Selecting at least one scan line L–L' from the image, the scan line L–L' is perpendicular to the image of the control line 11 and the target lines 12 to 16. A diagram of pixel value versus pixel position for the control lines 11 and the target lines 12 to 16 is thus established in accordance with the scan line L–L', see FIG. 7. The diagram of FIG. 7 shows three curves respectively representing the relationship of pixel value of R, G and B versus pixel position. Determining a color response R of the target line, such as the target line 13, from one of the three curves, for example the curve in blue pixels/or the combination of the three curves and in accordance with a formula (I):

$$R=\{(T-C)/(A-C)\}\times 100\% \quad (I),$$

wherein T represents an average pixel value of a section of pixels corresponding to the image of the target line 13, C represents an average pixel value of a section of pixels corresponding to the image of the control line 11, and A represents an average pixel value of a first section $A_1$ of pixels and a second section $A_2$ of pixels corresponding to the images of the base of the test strip 10 respectively adjacent to the image of the target line 13.

Then, at step 44, comparing the color response of the target line of the test strip with the setting value corresponding thereto derived from the mapping table corresponding to the test strip. At step 45, when the color response of the target line of the test strip is not smaller than the setting value, determining the target line has a positive test result (+) in response to one specific component in the test liquid and representing the specific component presents in the test liquid. When the color response of the target line of the test strip is less than the setting value, determining the target line has a negative test result (−) in response to the specific component and representing the specific component is absent in the test liquid. The test results for the target lines of the test strip determined by the present method are directly displayed on the data table 25 of the user interface of FIG. 2.

The present method detects the bar code corresponding to the test strip to obtain the type of the test strip. And, obtaining respective setting values of the target lines of the test strip in accordance with a mapping table of the setting values versus the target lines, which is correlated to the type of the test strip. Thereby, determining respective test results of the target lines of the test strip contacting with the test liquid by comparing the respective color responses of the target lines with the respective setting values. Hence, the present invention provides an automatic, rapid and accurate method to determine the test result of the probe zone of the test strip. The manual operation is eliminated and the detection time is shortened.

The embodiment is only used to illustrate the present invention, not intended to limit the scope thereof. Many modifications of the embodiment can be made without departing from the spirit of the present invention.

What is claimed is:

1. A method of automatically detecting a test result of a probe zone of a test strip, comprising:

providing a scanning object including a bar code and a plurality of test strips, said bar code placed in a predetermined position on said scanning object and said test snips arranged in sequence on said scanning object not overlapped with said bar code, each said test strip having a color pattern including a control line and a plurality of target lines arranged in sequence on said test strip from one end to the other end thereof, and said control line and each said target line respectively corresponding to a probe zone of said test strip;

scanning said scanning object to read a bar code pattern of said bar code and capture images of said test strips;

decoding said bar code pattern of said bar code to obtain information of types of said test strips and thereby a plurality of mapping tables of setting values versus positions of said target lines on one said test strip, each said mapping table corresponding to one said test strip based on the type of said test strip;

calculating a color response of one said target line of one said test strip based on the image of said test strip; and comparing the color response of said target line of said test strip with said setting value corresponding thereto derived from said mapping table corresponding to said test strip so as to determine whether said target line has a positive test result or a negative test result.

2. The method of claim 1, wherein the color response of said target line of said test strip is calculated in accordance with a formula (I):

$$R=\{(T-C)/(A-C)\}\times 100\% \quad (I),$$

wherein T represents on average pixel value of a section of pixels corresponding to the image of said target line, C represents an average pixel value of a section of pixels corresponding to the image of said control line, and A represents an average pixel value of a first section of pixels and a second section of pixels corresponding to the images of the base of said test strip respectively adjacent to the image of said target line.

3. The method of claim 2, wherein said color response R of said target line of said test strip is calculated based on the image of said test strip in red pixels.

4. The method of claim 2, wherein said color response R of said target line of said test strip is calculated based on the image of said test strip in green pixels.

5. The method of claim 2, wherein said color response R of said target line of said test strip is calculated based on the image of said test strip in blue pixels.

6. The method of claim 2, wherein said color response R of said target line of said test strip is calculated based on the image of said test strip in average pixels values of red, green, and blue pixels.

7. The method of claim 1, wherein said bar code has a one-dimensional bar code pattern, including:
   a first group of bar patterns corresponding to types of said test strips, each said bar pattern sequentially corresponding to the type of one said test strip;
   a plurality of second groups of bar patterns, each said second group of bar patterns sequentially corresponding to the position of one said target lines of said test strip; and
   a third group of bar patterns corresponding to an identification number of said scanning object.

8. The method of claim 7, wherein each said bar pattern of said bar code has a constant code length and consists of bars and spaces.

9. The method of claim 1, wherein said control line has a color change in response to a test liquid tested by said test strip and each said target line has a color change in response to a specific component in said test liquid.

10. The method of claim 9, wherein each said setting value of said mapping table corresponds to one said specific component to be detected by one said target line of said test strip.

11. The method of claim 10, wherein when the color response of said target line of said test strip is not smaller than said setting value, determining said target line having a positive test result in response to said specific component in said test liquid and representing said specific component present in said test liquid; when the color response of said target line of said test strip is less than said setting value, determining said target line having a negative test result in response to said specific component and representing said specific component absent in said test liquid.

12. The method of claim 9, wherein said test liquid includes a biological fluid collected from a subject.

13. The method of claim 12, wherein said biological fluid is selected from a group consisting of blood, urine, sweat and saliva.

14. The method of claim 1, wherein said test strip includes a drug abuse test paper.

15. An apparatus, comprising:
   a scanning object comprising a bar code and a plurality of test strips, wherein said bar code has a one-dimensional bar code pattern, including;
   a first group of bar patterns, at least one of said bar patterns corresponding to at least one type of a group of objects;
   a plurality of second groups of bar patterns, at least one of said second group of bar patterns corresponding to a set of setting values for said at least one type of group of objects; and
   a third group of bar patterns corresponding to an identification number of said scanning object;
   wherein at least some of said setting values correspond to at least some of said plurality of test strips.

16. The apparatus of claim 15, wherein said one-dimensional bar code pattern has a constant code length and consists of bars and spaces.

* * * * *